(12) United States Patent
Fischell et al.

(10) Patent No.: US 6,221,043 B1
(45) Date of Patent: Apr. 24, 2001

(54) STENT DELIVERY CATHETER WITH ENHANCED BALLOON SHAPE

(75) Inventors: Robert E. Fischell, Dayton, MD (US); David R. Fischell, Fair Haven, NJ (US); Tim A. Fischell, Richland, MI (US)

(73) Assignee: IsoStent, Inc., Dayton, MD (US)

( * ) Notice: Subject to any disclaimer, the term of this patent is extended or adjusted under 35 U.S.C. 154(b) by 0 days.

(21) Appl. No.: 09/373,552

(22) Filed: Aug. 13, 1999

(51) Int. Cl.$^7$ .................................................. A61M 29/00
(52) U.S. Cl. .................... 604/103.07; 604/96.01; 604/103.06; 604/916; 606/108; 606/194
(58) Field of Search ............................ 604/96.01, 103.05, 604/103.06, 103.07, 103.08, 915, 916; 606/108, 192, 198, 194; 623/1.11

(56) References Cited

U.S. PATENT DOCUMENTS

| | | | |
|---|---|---|---|
| 4,083,369 | * | 4/1978 | Sinnreich . |
| 5,254,091 | * | 10/1993 | Aliahmad et al. . |
| 5,334,146 | * | 8/1994 | Ozasa . |
| 5,338,298 | * | 8/1994 | McIntyre . |
| 5,470,313 | * | 11/1995 | Crocker et al. . |
| 5,769,871 | * | 6/1998 | Mers Kelly et al. . |

\* cited by examiner

Primary Examiner—John G. Weiss
Assistant Examiner—LoAn H. Thanh

(57) ABSTRACT

Disclosed is a balloon on a distal portion of a balloon angioplasty catheter. The section of the balloon onto which a stent can be mounted has a central segment that is substantially cylindrical in shape that is centered between two segments each having the shape of a sector of a prolate spheroid. This shape for a balloon for a stent delivery catheter provides a more cylindrical shape for the stent after it is implanted in an artery that has a typical distribution of plaque in an arterial stenosis, which distribution of plaque is greatest for some limited length at a central region of the stenosis and then decreases somewhat uniformly as one approaches the edges of the stenosis. Another embodiment of the invention utilizes two segments that are frustums of a cone instead of sectors of a prolate spheroid, which conical segments surround the central cylindrical segment. Also disclosed is a balloon whose compliance decreases continuously as a function of the distance away from either end of the central segment. Any of these embodiments can employ dual conical end segments at each end of the balloon which consist of two adjacent frustums of a cone making different half-angles with the longitudinal axis of the balloon.

8 Claims, 5 Drawing Sheets

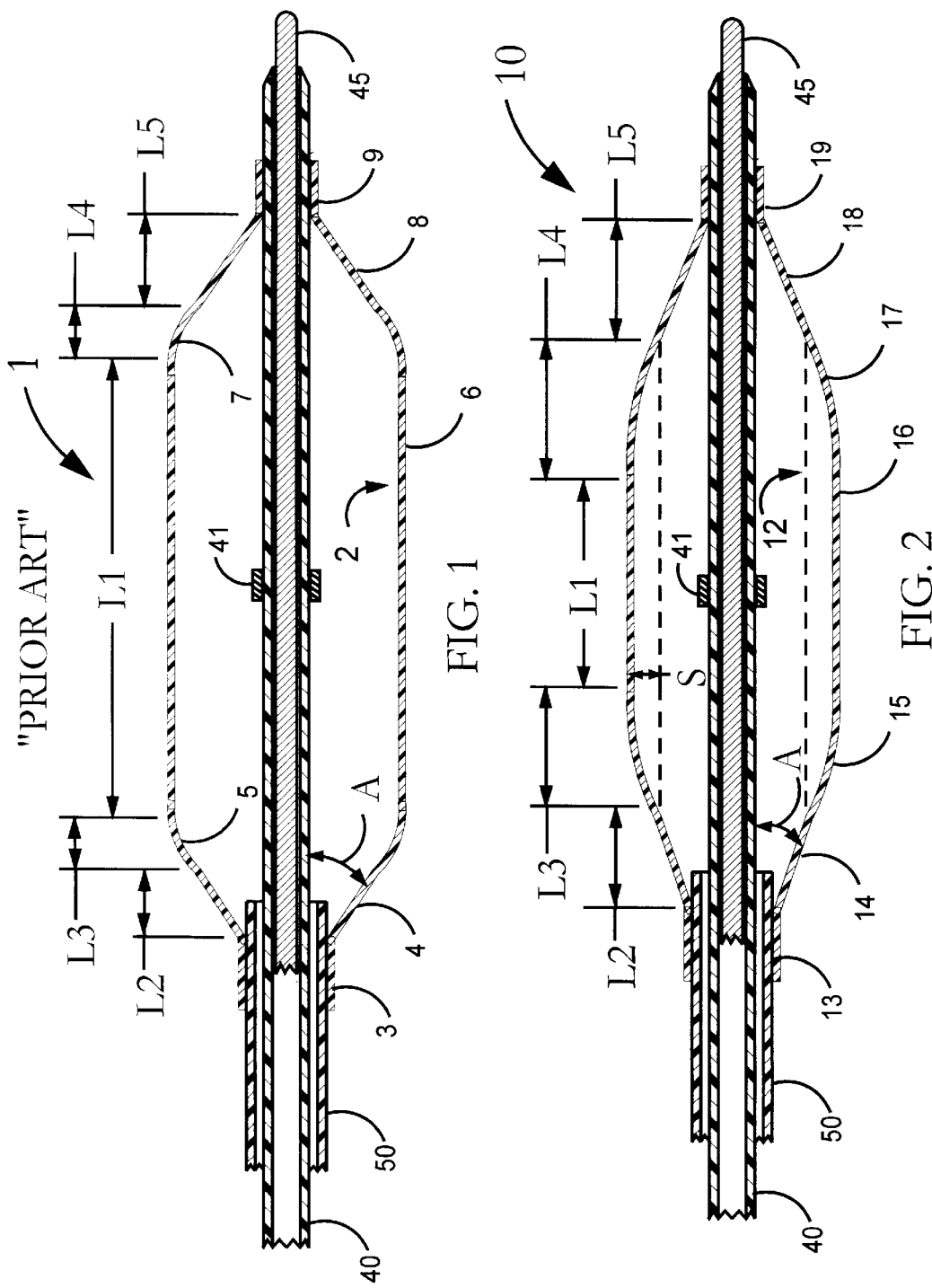

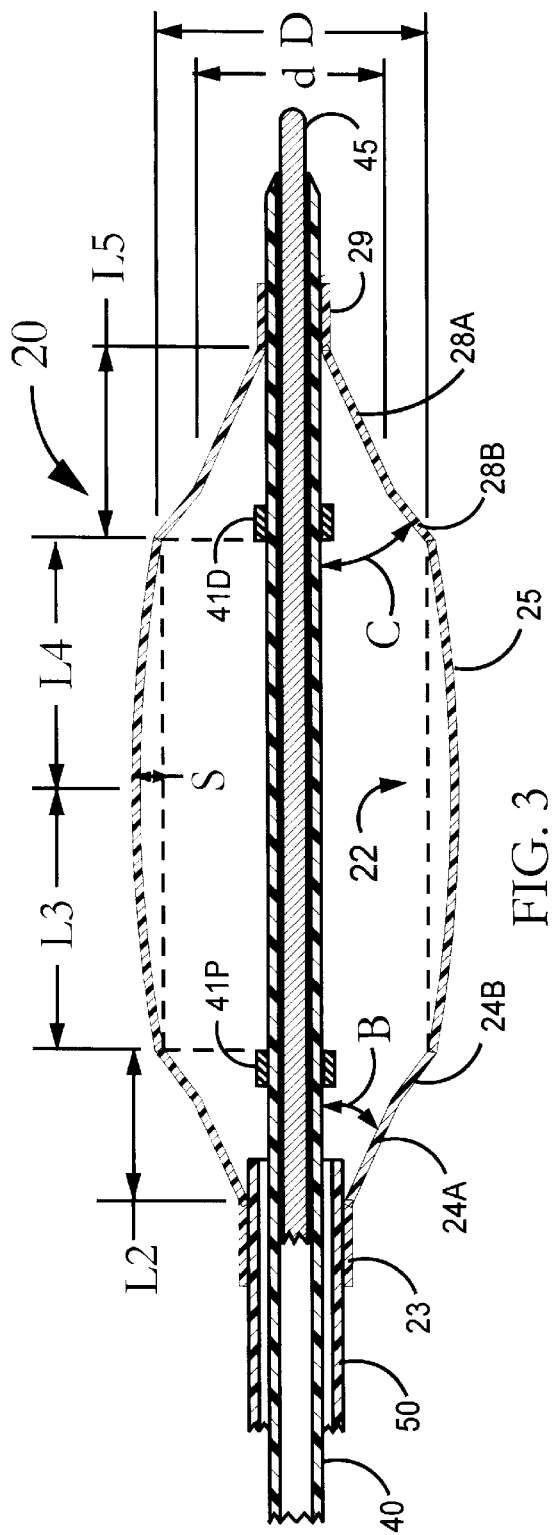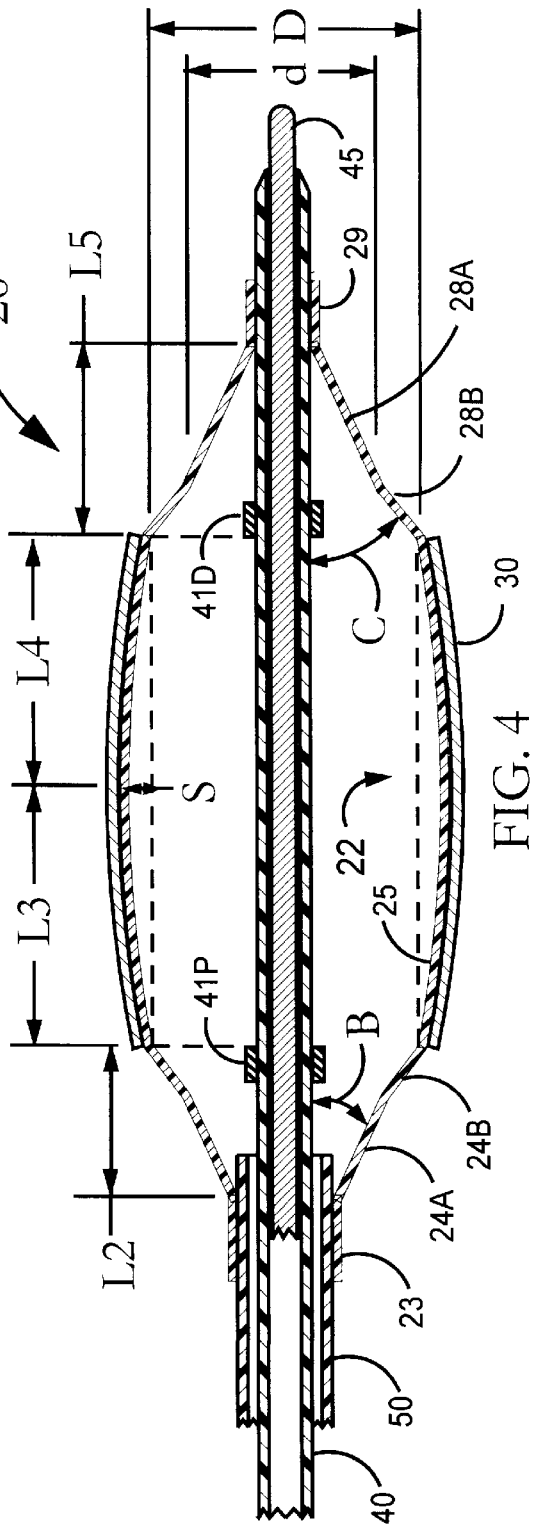

STENT DELIVERY CATHETER WITH ENHANCED BALLOON SHAPE

FIELD OF USE

This invention is in the field of devices for delivering stents into a vessel of a human body. More specifically, this invention is an angioplasty balloon that has an inflated shape that is ideally suited for delivering a stent into a stenosis of an artery or for performing balloon angioplasty.

BACKGROUND OF THE INVENTION

Balloon expandable stents have for many years been mounted on angioplasty balloons situated at a distal portion of a balloon angioplasty catheter. When the balloon is inflated at the site of an arterial stenosis, the stent is expanded radially outward thus acting as a scaffold to keep the stenosis from closing after the balloon is deflated and removed from the body. To accomplish this objective, prior art balloons utilize a cylindrical section that extends along most of the longitudinal length of the balloon. A stent is then co-axially mounted at the longitudinal center of this cylindrical section. Because there is typically more resistance to the expansion of the stent at its longitudinal center (as compared to the ends of the stent where there is comparatively little plaque) a deployed stent tends to have an undesirable hourglass shape. That is, pressure from excessive plaque at the longitudinal center of the stent causes that region of the stent to have a reduced diameter.

This problem was addressed in the invention by M. Crocker et al that is disclosed in U.S. Pat. No. 5,843,116. The Crocker et al invention has a longitudinally centered, comparatively short, cylindrical segment that has an increased diameter as compared to the diameter of the balloon cylindrical segments situated both proximal and distal to that central cylindrical segment. Thus, a stent deployed on such a balloon would have an increased diameter at the longitudinal center of the stent. However, it would be extremely rare for a stenosis to have a longitudinal distribution of plaque that is exactly cylindrical for about one third of the longitudinal length of the stent and then becomes a cylindrically shaped, uniformly reduced extent of the plaque both proximal and distal to that center segment. More typically, the plaque has its greatest volume at a central region of a stenosis and then rather uniformly decreases in the extent of the plaque as one moves away from that central region in either a proximal or a distal direction. Thus the Crocker et al invention that has discontinuous (i.e. abrupt) changes in balloon compliance along the length of the balloon is not ideally suited for the placement of a stent in a typical arterial stenosis.

Another problem associated with stents is called "balloon overhang". Balloon overhang is the length of an inflated balloon that extends beyond the edge of the radially expanded balloon. For example, if a radially expanded stent is 17 mm long and mounted on a balloon that has a length when inflated of 20 mm, then the balloon overhang at each end of the stent is 1.5 mm. It has been found in actual practice that a large percentage of restenosis after stent implantation occurs in the region just proximal and just distal to the edge of the stent. This phenomenon, which is known as the "edge effect", is even more pronounced with a radioisotope stent such as described in U.S. Pat. No. 5,059,166 by Fischell et al. One explanation for the edge effect is that trauma to the arterial wall caused by the balloon results in late vascular contraction at that region; and there is no stent structure in that region of balloon overhang to act as a scaffold to prevent the late vasculature contraction.

Prior art balloons all have a conical segment placed at each end of the balloon. The proximal conical end segment is joined at its proximal end to the outer shaft of a stent delivery catheter or balloon angioplasty catheter. The distal conical end segment is joined at its distal end to the distal end of the inner shaft of a balloon angioplasty catheter which balloon angioplasty catheter can also be used for delivering a stent. Early designs for conical end segments had half-angles that were about 45 degrees. Although this half-angle provides a desirable sharp corner where the conical segment joins the cylindrical segment of the balloon, this comparatively high 45 degree half-angle makes it somewhat more difficult for the balloon to be advanced through tortuous coronary vasculature. Therefore, more recent balloon designs have a half-angle for the conical segments that is typically less than 20 degrees. Although this decreased half-angle provides for improved tracking through small curved arteries, the exact length of the cylindrical segment of the balloon onto which a stent would be mounted is more difficult to ascertain. This can lead to a greater length of balloon overhang that results in an increased level of trauma and restenosis beyond the edges of the stent. That is, this can lead to the undesirable result of an increased edge effect.

SUMMARY OF THE INVENTION

The objectives of this invention are to overcome several of the shortcomings of prior art balloons as used for balloon angioplasty or as used for delivering a stent into a vessel of a human body.

In a first embodiment of the present invention, a balloon is disclosed that has a longitudinally centered central segment that has a substantially cylindrical shape. The length of this central segment is less than one third of the nominal length of the expanded balloon. Immediately proximal to the central segment of the balloon is a proximal segment of the balloon in the form of a prolate spheroid having a distal end that is the same diameter as the diameter of the cylindrical central segment and a proximal end that has a slightly reduced diameter. Immediately distal to the central segment is a distal segment in the form of a prolate spheroid that has the same diameter as the central segment at its proximal end and a slightly decreased diameter at its distal end. Thus, the section of the balloon onto which the stent is mounted has a central segment that is substantially cylindrical in shape that is centered between two prolate spheroids. This shape for a balloon for a stent delivery catheter provides a more cylindrical shape for the stent after it is implanted in an artery that has a typical distribution of plaque, which distribution of plaque is greatest for some limited length at a central region of the stent and then decreases somewhat uniformly as one approaches the edges of the stent. This balloon shape would also be suitable for the balloon of a balloon angioplasty catheter.

In what could be considered a second embodiment of the present invention, the length of the cylindrical central segment is zero. That is, the distal end of the proximal prolate spheroid balloon segment is fixedly joined to the proximal end of the distal prolate spheroid segment with no cylindrical segment in between. This design is particularly suitable for stent delivery or for balloon angioplasty if the plaque in a stenosis that is being treated has a greatest extent at the center of the stenosis and decreases somewhat uniformly in the extent of the plaque as one approaches the ends of the balloon.

Another embodiment of the present invention, is similar to the first or second embodiment except that the segments that have a prolate spheroid shape are replaced with conical segments whose actual shape is a frustrum of a cone.

Another embodiment of the present invention is a balloon having the same general shape as described for the first two embodiments described above. However, the third embodiment has a central, substantially cylindrical segment having a thinner wall thickness as compared to the average wall thickness of the prolate spheroid segments. In a particular embodiment, where the prolate spheroid segments join the cylindrical central segment, both prolate spheroid segments have the same wall thickness at their junction points with the central segment. Then, as one approaches the ends of the balloon, the wall thickness of both the proximal and distal prolate spheroid segments increase continuously to a maximum wall thickness where each prolate spheroid segment joins a conical end segment at each end of the balloon. This has the effect of decreasing the compliance of the balloon as one moves from a region of maximum compliance at the central segment of the balloon to a region of minimum compliance as one approaches each end of the balloon. Thus, at a nominal inflation pressure of, let us say, 12 atmospheres, the center of the balloon could have a diameter of 3.2 mm and each end of the prolate spheroid segment that joins the balloon's conical segment could have a diameter of 3.0 mm. Because of a decreased compliance as one moves outward from the longitudinal center of the balloon, when the pressure would be increased to 16 atmospheres, the center of the balloon could go to a diameter of 3.5 mm while the ends of each prolate spheroid segment might only increase in diameter to 3.1 mm. Thus the center bulge of the balloon would increase from 0.2 mm at 12 atmospheres to 0.4 mm at 16 atmospheres. This balloon characteristic is useful in adapting the balloon for the treatment of stenoses having different distributions of plaque within such stenoses.

In another embodiment of the present invention, the wall thickness of the balloon would remain uniform but the compliance of the balloon material would decrease as one moves away from the longitudinal center of the balloon. This type of balloon could be made by using a balloon material whose compliance could be decreased by increased exposure to ionizing radiation such as gamma ray radiation. Thus, the central segment of the balloon would receive no radiation and the level of radiation exposure of the balloon would then increase as one moves toward each end of the balloon. This type of construction would have the same effect as increasing the wall thickness of the balloon as one moves toward each end of the balloon, which was the embodiment of the present invention described in the preceding paragraph.

An additional aspect of the design of the balloons of the present invention involves the end segments of the balloon that are generally conical in shape. More accurately, each end segment has the shape of a frustrum of a cone. These conical end segments join the prolate spheroid segments to the inner or outer shafts of the balloon angioplasty catheter. That is, the conical end segments are at the ends of the balloon. Prior art balloons have conical end segments that have a single half-angle that is typically between 15 and 45 degrees. One embodiment of present invention has end segments that are dual conical end segments. That is, the half-angle of the longitudinally outermost portion of the dual conical end segment is between 10 and 25 degrees, and the half-angle of the longitudinally innermost portion of the dual conical end segment has a half-angle between 40 and 70 degrees. Because the innermost portion of the dual conical segments has a comparatively large half-angle, this design provides a well defined length of the balloon onto which length a stent can be mounted. By controlling the length of the stent as compared to a well defined length of the balloon in the region where the stent is mounted, balloon overhang can be reduced. By having the outermost portion of the conical end segment being cone-shaped with a minimum cone half-angle, the balloon will provide the desirable attribute of good tracking through tortuous coronary arteries. Thus a dual conical end segment for the balloon has distinct advantages over prior art designs.

Thus an object of the present invention is to have a central segment of a balloon of a stent delivery catheter or a balloon angioplasty catheter have its greatest diameter at the longitudinal center of the balloon; the central segment being substantially cylindrical and having a length that is less than one third the nominal length of the balloon.

Another object of the present invention is to have a substantially cylindrical central segment of a balloon that is placed between two elongated prolate spheroid segments; the total length of the prolate spheroid segments being greater than the length of the central cylindrical segment.

Still another object of the present invention is to have a substantially cylindrical central segment of a balloon that is placed between two elongated conical segments; the total length of the conical segments being greater than the length of the central cylindrical segment.

Still another object of the present invention is to have each end segment of the balloon to be in the form of a dual conical end segment.

Still another object of the present invention is to have a balloon for a balloon angioplasty catheter that has a maximum compliance at a central segment of the balloon and a continuously decreasing compliance as one moves away from that central segment towards the edges of the balloon.

These and other important objects and advantages of this invention will become apparent from the detailed description of the invention and the associated drawings provided herein.

BRIEF DESCRIPTION OF THE DRAWINGS

FIG. 1 is a longitudinal cross section of a prior art balloon situated at a distal portion of a balloon angioplasty catheter.

FIG. 2 is a longitudinal cross section of a first embodiment of the present invention that has a decreased length of a cylindrical central segment as compared to prior art balloons.

FIG. 3 is a longitudinal cross section of a second embodiment of the present invention wherein the balloon has a zero length of the cylindrical central segment and an increased length of the proximal and distal prolate spheroid segments. This balloon design also has end conical segments that have two different half-angles; i.e., these are dual conical end segments.

FIG. 4 is a longitudinal cross section of a stent mounted onto an inflated balloon having the design shown in FIG. 3 with the balloon being inflated without any external resistance from a stenosis.

DETAILED DESCRIPTION OF THE INVENTION

Figure 5:
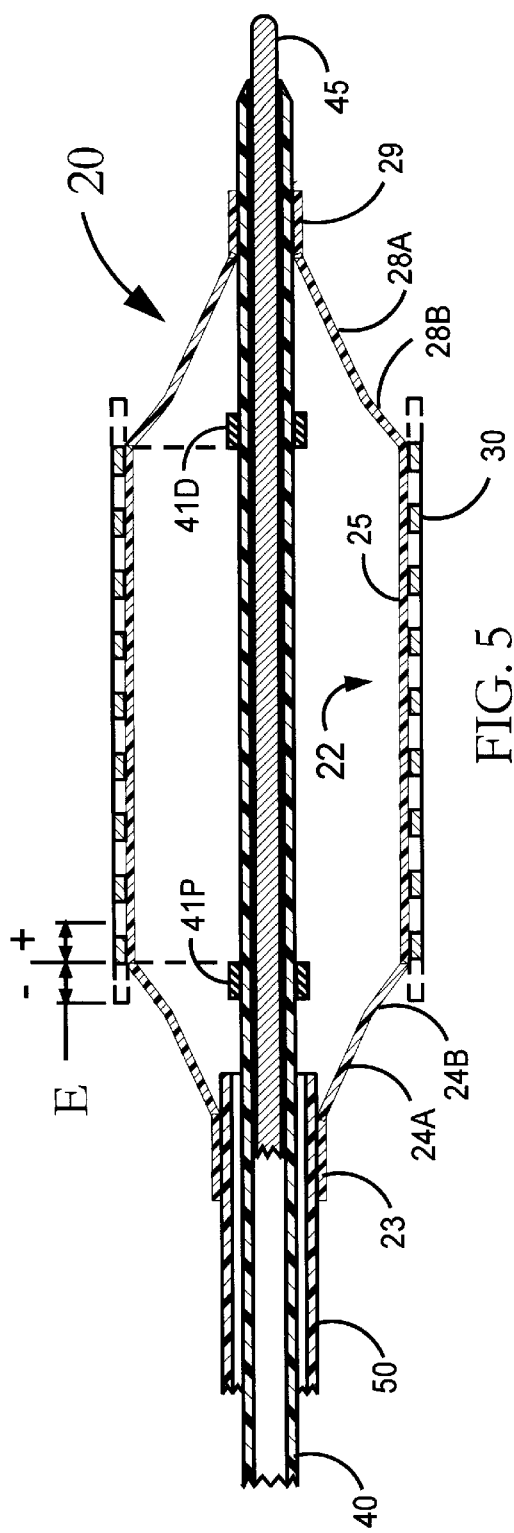
FIG. 5 is a longitudinal cross section of the embodiment of FIG. 4 showing the resulting shape of the stent when the balloon of FIG. 4 is inflated into a stenosis having a greater extent of plaque at the longitudinal center of the stenoses.

FIG. 1 is a longitudinal cross section of a distal portion of a prior art balloon angioplasty catheter 1 having a balloon 2 with its proximal end fixedly attached to the distal end of the catheter's outer shaft 50 and the distal end of the balloon 2 being fixedly attached to the distal end of the inner shaft 40. The inner shaft 40 has a central lumen through which a guide wire 45 can be slideably placed. A radiopaque marker band 41 is typically attached to the inner shaft 40 at the longitudinal center of the balloon 2. The balloon 2 has a central segment 6 having a length L1 that is typically most of the total length of the balloon 2. Just proximal to the central segment 6 is a short, proximal segment 5 in the form of a prolate spheroid having a longitudinal length L3. Just distal to central segment 6 is a distal segment 7 also in the form of a prolate spheroid having a length L4.

Typically, the length L3 equals the length L4. Just proximal to the proximal segment 5 is a proximal conical end segment 4 having a longitudinal length L2. The proximal end segment 4 is joined to a cylindrical segment 3 that is fixedly attached to the outer shaft 50 of the balloon angioplasty catheter 1. Just distal to the distal segment 7 is a distal conical end segment 8 having a length L5. The distal end segment 8 is joined to a cylindrical segment 9 that is fixedly attached to the inner shaft 40. The conical end segments 4 and 8 each have a half-angle "A" with respect to the longitudinal axis of the balloon. The angle "A" is typically between 15 and 45 degrees. The length L1 is typically at least twice the sum of the lengths L3 plus L4.

FIG. 2 is a first embodiment of the present invention which is a balloon angioplasty catheter 10 having a distal portion onto which is mounted a balloon 12 having a central segment 16 which has a length L1. Just proximal to the central segment 16 is an elongated proximal segment 15 having a length L3. Just distal to the central segment 16 is an elongated distal segment 17 having a length L4. Both the proximal segment 15 and the distal segment 17 have the shape of a prolate spheroid. Just proximal to the proximal segment 15 is a conical end segment 14 having a longitudinal length L2 and a half-angle "A" with respect to the longitudinal axis of the balloon 12. The conical segment 14 is joined to the cylindrical segment 13 that is fixedly attached to the outer shaft 50 of the balloon angioplasty catheter 10. Just distal to the distal segment 17 is a conical segment 18 having a length L5 and typically the same half-angle "A". The conical end segment 18 is joined to a cylindrical segment 19 that is fixedly attached to the distal end of the inner shaft 40.

The embodiment of the present invention shown in FIG. 2 is characterized by having a length L1 of the central segment 16 that is comparatively short as compared to the length L1 of the central segment 6 of the prior art balloon 2. This also requires that the lengths L3 and L4 of the elongated prolate spheroid segments 15 and 17 of the balloon 10 are much longer as compared to the segments 5 and 7 of the prior art balloon 2. The FIG. 2 embodiment of the present invention can be characterized as having a length L1 that is shorter than the sum of the lengths L3 plus L4; i.e., L1<L3+L4. The prior art balloon 2 is characterized by having the length L1 being greater than twice the sum of the lengths L3 plus L4: i.e., L1>2×(L3+L4).

A typical design for the balloon 12 having a nominal balloon length of L1+L3+L4=20 mm would have L1=5 mm and L3+L4=15 mm. For the balloon 12, if L1+L3+L4=30 mm, typical dimensions would be L1=5 mm and L3+L4=25 mm with L3=L4=12.5 mm. For the prior art balloon 2, if L1+L3+L4=30 mm, then typically L1=26 mm and L3=L4=2 mm. It should also be noted that the lengths L3 and L4 are typically equal; i.e. L3=L4.

The embodiment of the present invention shown in FIG. 2 would have the advantage over the design of the Crocker et al patent in that the prolate spheroid segments 15 and 17 would be able to provide a more cylindrical final arterial lumen for stent deployment or for balloon angioplasty because of better matching of the shape of the balloon 12 with the typical distribution of plaque in an arterial stenosis.

It should be understood that the segments 15 and 17 are not a complete prolate spheroid, (a complete prolate spheroid being the general shape of a U.S. football) but rather only a comparatively short sector of a complete prolate spheroid. Furthermore, the segments 15 and 17, though having a substantially prolate spheroidal shape, can, within the scope of this invention, deviate somewhat from that general shape.

FIG. 3 illustrates a second embodiment of the present invention that is really a special case of the first embodiment shown in FIG. 2. The FIG. 3 embodiment has a length L1=0; i.e., the proximal segment of length L3 is joined to the distal segment of length L4 to form a single prolate spheroid segment 25 having a length equal to the sum of L3 plus L4. At the longitudinal center of the balloon 22, the bulge or deflection "S" indicates the increased radial distance at the longitudinal center of the balloon 22 as compared to a cylinder whose radius would be the same as radius of the prolate spheroid segment 25 at its proximal and distal ends. The dimension "S" would typically be between 5% and 15% of the maximum diameter of the balloon 22. A typical value of "S" for a 3 mm diameter balloon would be approximately 0.25 mm.

The balloon 22 of FIG. 3 is mounted on a distal portion of the balloon angioplasty catheter 20. The central prolate spheroid segment 25 is joined at its proximal end to a first conical segment 24B which is joined to a second conical segment 24A that is joined to a cylindrical segment 23 that is fixedly attached to the outer shaft 50 of the balloon angioplasty catheter 20. The central prolate spheroid segment 25 is joined at its distal end to a first conical segment 28B that is joined to a second conical segment 28A that is joined to a cylindrical segment 29 that is fixedly attached to the distal end of the inner shaft 40. Thus at the proximal end of the balloon 22 is a dual conical end segment consisting of a first conical segment 24B that makes a half-angle "C" with the longitudinal axis of the balloon 22 and a second conical segment 24A having a half-angle "B" with the longitudinal axis of the balloon 22. The sum of the longitudinal lengths of the conical segments 24A and 24B is L2. At the distal end of the balloon 22 is another dual conical end segment consisting of a first conical segment 28B that makes a half-angle "C" with the longitudinal axis of the balloon 22 and a second conical segment 28A that makes a half-angle "B" with the longitudinal axis of the balloon 22. The sum of the longitudinal lengths of the conical segments 28A and 28B is L5. Also from FIG. 4 it is seen that the maximum diameter of the conical segments 24A and 28A is the dimension "d" and the maximum diameter of the conical segments 24B and 28B is the dimension "D". The difference between the dimensions "D" and "d" would typically be between 0.2 and 2.0 mm with an optimum value for arterial stenting of approximately 1.0 mm.

Although the balloon of FIG. 3 shows the dual conical end segments with a novel design for the central segment of the balloon, it should be understood that the unique and novel advantages of dual conical end segments could be used with a conventional balloon having a substantially cylindrical central segment as shown in FIG. 1.

To make a sharp corner along the circle where the ends of the central segment 25 join to the first conical segments 24B and 28B, it is necessary for the half-angle "C" to be greater than 40 degrees and typically between 40 and 70 degrees. A sharp corner is highly desirable in order to have a well defined longitudinal length for the central segment 25. A well defined length for the central segment 25 is desirable so the length of the stent 30 (as shown in FIG. 4) can be matched to the length of the central segment 25 with the goal of minimizing the length of balloon overhang. Decreasing the length of balloon overhang will reduce the extent of late vasculature contraction just beyond the edges of the stent thus reducing the risk of having restenosis just beyond the ends of the stent. That is, minimum balloon overhang will decrease the edge effect.

The conical segments 24A and 28A would ideally have a half-angle "B" between 10 and 25 degrees. A smaller half-angle "B" provides better tracking of the balloon angioplasty catheter 20 as it is advanced through tortuous coronary arteries. Thus, the dual conical segment design can provide good tracking of the catheter 20 while at the same time providing a well defined length of the central segment 25 having sharp corners where the first conical segments 24B and 28B join to the central segment 25.

FIG. 4 shows a stent 30 deployed in air on the inflated balloon 22. The stent 30 in FIG. 4 is shown with essentially zero length of balloon overhang which is an ideal condition for deploying a stent in an artery of a human subject.

Also shown in FIGS. 3 and 4 is a proximal radiopaque marker band 41P and a distal radiopaque marker band 41D. As shown in FIG. 4, these marker bands can be placed on the inner shaft 40 at positions where they will indicate the deployed length of the stent 30.

Figure 8:
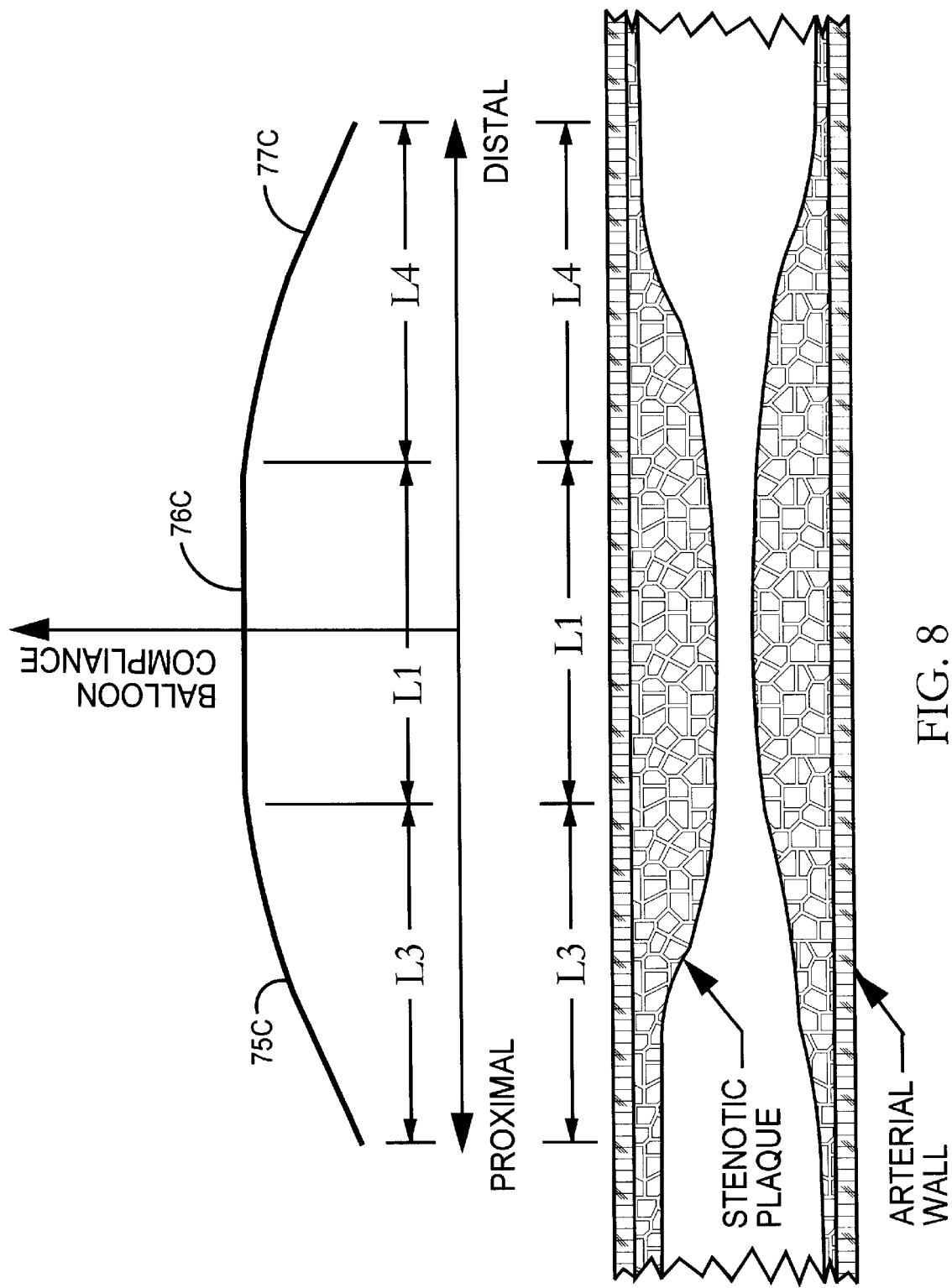
FIG. 8 shows a typical arterial stenosis and also illustrates how regions of a balloon's variable compliance would correspond to a varying extent of plaque in that stenosis.

FIG. 5 is a longitudinal cross section of a distal portion of the balloon angioplasty catheter 20 which shows the shape of the stent 30 as it would be deployed in an artery that has the greatest extent of plaque in a region around the longitudinal center of the stent 30 with continuously decreasing extent of the plaque as one approaches the ends of the stent 30. That is, the greatest resistance to the expansion of the balloon 22 and stent 30 is at a region around their longitudinal centers. Thus, when expanded in a typical arterial stenosis (as seen at the bottom of FIG. 8), the stent 30 would have a substantially cylindrical shape as is shown in FIG. 5. Furthermore, by matching the length of the deployed stent 30 with the length of the central segment 25, ideally one can approach a zero length of balloon overhang. Because of manufacturing variations in the actual lengths of the central segment 25 and the stent 30, there will be a variation of ±"E" in the extent of balloon overhang. With carefully controlled processes, the magnitude of "E" can be held to less than±1.0 mm.

Figure 6:
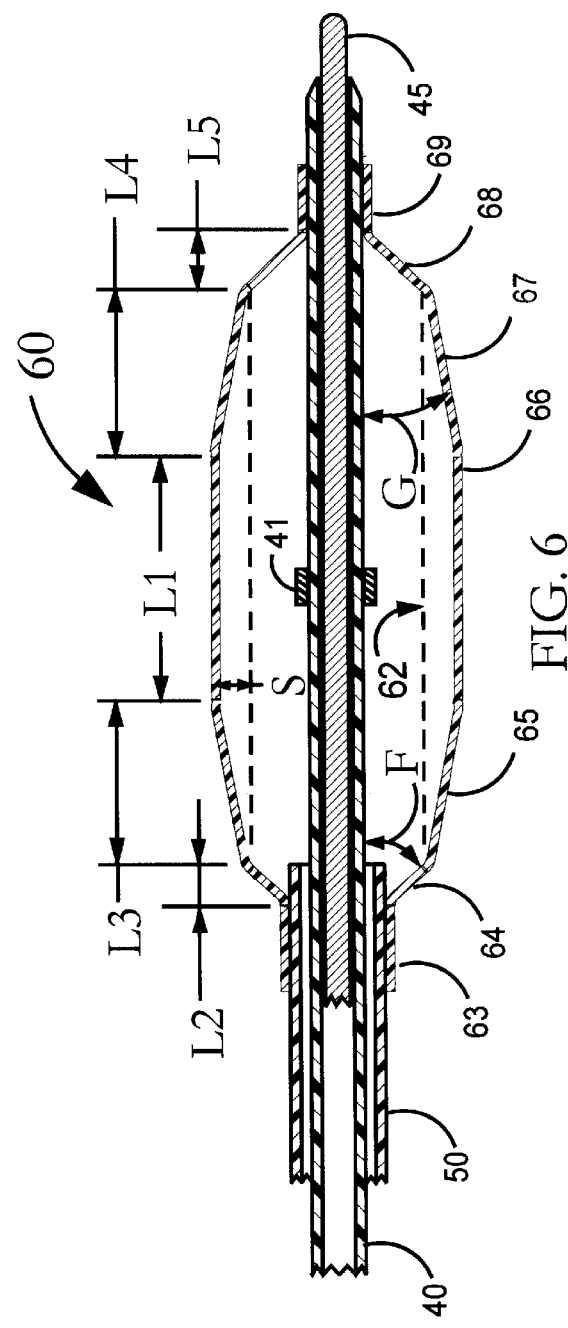
FIG. 6 is an longitudinal cross section of a balloon that has a cylindrical central segment between proximal and distal conical segments each having the shape of a frustrum of a cone.

FIG. 6 is another embodiment of the present invention that is similar to the first embodiment as shown in FIG. 2. FIG. 6 shows a balloon 62 mounted at a distal portion of a balloon angioplasty catheter 60. The substantially cylindrical central segment 66 is joined at its proximal end to a proximal conical segment 65 that is joined to a conical end segment 64 that is joined to a cylindrical segment 63 that is fixedly attached to the distal end of the outer shaft 50. The distal end of the central segment 66 is joined to a distal conical segment 67 that is joined to a conical end segment 68 that is joined to a cylindrical segment 69 that is fixedly attached to the distal end of the inner shaft 40. The conical end segments 64 and 68 make an angle "F" with the balloon's longitudinal axis. The angle "F" could be between 15 and 45 degrees. The proximal and distal conical segments 65 and 67 make an angle "G" with the balloon's longitudinal axis. The angle "G" would typically be between 1 and 10 degrees. As with the balloon 12 of FIG. 2, the balloon 62 is characterized by having the length L1<L2+L3. It should be understood that the actual shape of the proximal and distal conical segments 65 and 67 would be substantially a frustum of a cone. Further it should be understood that dual conical end segments as shown in FIGS. 3, 4 and 5 could be used for the embodiment of FIG. 6 instead of the single conical end segments shown in FIG. 6.

Figure 7:
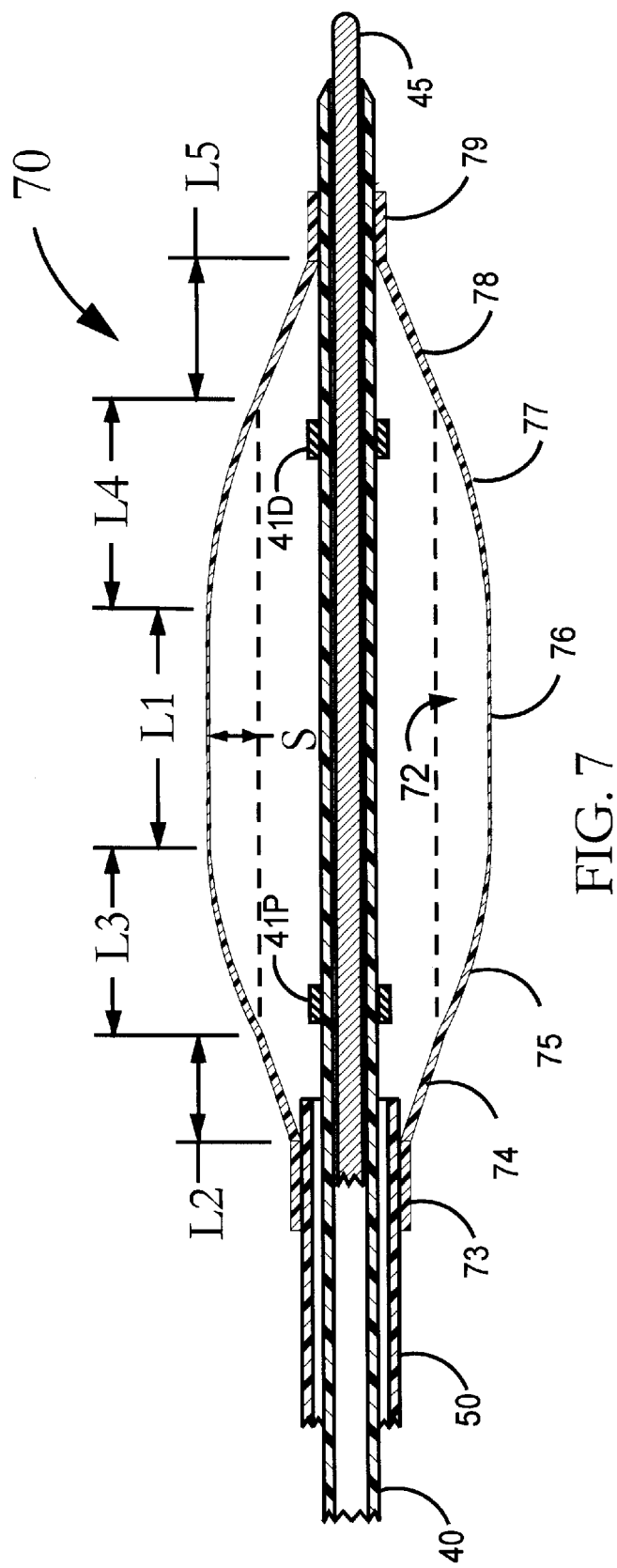
FIG. 7 is a longitudinal cross section of a balloon that has a minimum wall thickness at a longitudinally centered segment of the balloon with increasing wall thickness as one moves toward each end of the balloon.

FIG. 7 is a longitudinal cross section of a distal portion of a balloon angioplasty catheter 70 having a balloon 72 that has increasing wall thickness as one moves away from the central substantially cylindrical segment 76. Thus the segment 76 would have a minimum wall thickness (e.g., 0.05 mm) throughout its length. The elongated prolate spheroid segments 75 and 77 would have the same wall thickness as the central segment 76 where they are joined to the central segment 76. The thickness of the prolate spheroid segments 75 and 77 would increase as one moves toward the ends of the balloon 72. This increase in wall thickness as one approaches either end of the balloon 72 can also be true for the conical end segments 74 and 78 which are joined respectively to the cylindrical segments 73 and 79. Typically the cylindrical segments 73 and 79 would have the greatest wall thickness.

The design shown in FIG. 7 has the interesting attribute that the compliance of the balloon 72 decreases as one moves outward from the ends of the central segment 76 toward the ends of the balloon 72. Thus, at a nominal pressure such as 12 atmospheres, the deflection distance "S" would be considerably less than the deflection distance "S" at a balloon pressure of 16–20 atmospheres. Thus an interventional cardiologist using the balloon angioplasty catheter 70 could adjust the extent to which the central segment 76 pushes out against an arterial stenosis as compared to the outward push from the prolate spheroid segments 75 and 77. This could be particularly important when deploying a stent mounted onto the balloon 72. Thus, the cardiologist could steadily increase the balloon pressure until the stent shape, when the balloon is deflated, is the ideal cylindrical shape as shown in FIG. 5. For this embodiment of the present invention as shown in FIG. 7, the length L1 is ideally less than the sum of the lengths L3 plus L4.

Shown at the bottom of FIG. 8 is a typical distribution of stenotic plaque within a stenosis in an artery of a human subject. Shown at the top of FIG. 8 is a near optimum shape of the compliance of a balloon as a function of the distance away from the longitudinal center of the balloon such as the balloon 72 of FIG. 7. Thus the central region of the length of L1 has a maximum balloon compliance 76C. As one moves outwardly from the ends of the central region 76 of balloon 72, the balloon compliance continuously decreases as shown at the top of FIG. 8 by the decreasing compliance curve 75C having a length L4 and the curve 77C having a length L4.

For the typical stenotic plaque distribution shown at the bottom of FIG. 8, and with the balloon of FIG. 7 having the balloon compliance curves shown at the top of FIG. 8, a near ideal result for a deployed stent 30 as seen in FIG. 5 can be obtained.

Still another embodiment of the present invention can be represented by the drawing of FIG. 2. Specifically, if the balloon 12 of FIG. 2 had an increased durometer of the material of the balloon 16 as one moves from the ends of the central segment 16 toward the ends of the balloon 12, then there would be a decreased compliance of the balloon 12 as one moves toward the ends of the balloon 12. Thus the compliance of the balloon 12 as a function of longitudinal distance from the ends of the central segment 16 would be conceptually the same as the compliance of the balloon 72 of FIG. 6; which balloon compliance curve is shown at the top of FIG. 8. Of course the balloon 72 of FIG. 6 could also have both an increased durometer and increased wall thickness of the balloon material as one approaches the ends of the balloon 72 to further enhance the decrease of balloon compliance as one approaches the ends of the balloon 72.

One method for increasing the durometer of the balloon material would be by exposing the balloon material to an increasingly high level of ionizing radiation as one moves away from the ends of the balloon's central segment 16 (or 76). For example, if an inflated balloon was placed in an apparatus that completely prevented gamma ray exposure of the central segment 16 of FIG. 2 while providing continuously increasing exposure to gamma rays as one moves from the central segment 16 toward the edges of the balloon, then a balloon having the compliance characteristics as shown at the top of FIG. 8 could be created. This design would have the advantages of the design of FIG. 7, but it would have a uniform wall thickness for the balloon. A uniform balloon thickness would have the advantage of being less difficult to manufacture. The desired non-uniform irradiation of the balloon could be accomplished by exposing, the balloon to a gamma ray source while completely shielding the central segment 16 and using a decreasing thickness of radiation shielding as one moves from the ends of the central segment 16 toward the ends of the stent. The effect of increased radiation is to increase cross linking of the polymer of the balloon material, thus decreasing balloon compliance.

Various other modifications, adaptations, and alternative designs are of course possible in light of the above teachings. Therefore, it should be understood at this time that within the scope of the appended claims the invention may be practiced otherwise than as specifically described herein.

What is claimed is:

1. An inflated balloon situated at a distal portion of a balloon angioplasty catheter, the balloon having an elongated proximal spheroid segment that has a proximal end, a distal end and a length L3, the balloon also having an elongated distal spheroid segment that has a proximal end, a distal end and a length L4, the proximal spheroid segment and the distal spheroid segment each having substantially the shape of a sector of a prolate spheroid, the balloon also having a central segment that has a proximal end, a distal end and a length L1, the central segment having a substantially cylindrical shape, the distal end of the proximal spheroid segment being joined to the proximal end of the central segment and the proximal end of the distal spheroid segment being joined to the distal end of the central segment, the balloon being characterized by having the length of the central segment being less than the sum of the lengths of the proximal spheroid segment and the distal segment which can be written as L1<L3+L4, the balloon being further characterized by having a proximal end segment and a distal end segment each having a proximal end and a distal end and each having the general shape of a frustrum of a cone, the distal end of the proximal end segment being joined to the proximal end of the proximal spheroid segment and the proximal end of the distal end segment being joined to the distal end of the distal spheroid segment.

2. The balloon of claim 1 wherein the proximal end segment is a proximal dual conical end segment having a proximal end and a distal end and the distal end segment is a distal dual conical end segment having a proximal end and a distal end, the distal end of the proximal dual conical end segment being joined to the proximal end of the balloon's proximal spheroid segment and the proximal end of distal dual conical end segment being joined to the distal end of balloon's distal spheroid segment, each dual conical end segment being characterized by having the shape of a first frustum of a cone that makes an angle "C" with the balloon's longitudinal axis, and a second frustum of a cone that makes an angle "B" with the balloon's longitudinal axis, the angle "C" being greater than the angle "B".

3. The balloon of claim 2 wherein the angle "B" is between 10 and 25 degrees.

4. The balloon of claim 2 wherein the angle "C" is between 40 and 70 degrees.

5. The balloon of claim 1 wherein the length L3 is approximately equal to the length L4.

6. An inflated balloon onto which a metal stent is coaxially placed, the balloon and the stent both being situated at a distal portion of a balloon angioplasty catheter, the balloon having an elongated proximal spheroid segment that has a proximal end, a distal end and a length L3, the balloon also having an elongated distal spheroid segment that has a proximal end, a distal end and a length L4, the proximal spheroid segment and the distal spheroid segment each having substantially the shape of a sector of a prolate spheroid, the balloon also having a central segment that has a proximal end, a distal end and a length L1, the central segment having a substantially cylindrical shape, the distal end of the proximal spheroid segment being joined to the proximal end of the central segment and the proximal end of the distal spheroid segment being joined to the distal end of the central segment, the balloon being characterized by having the length of the central segment being less than the sum of the lengths of the proximal spheroid segment and the distal segment which can be written as L1<L3+L4, the balloon being further characterized by having a proximal end segment and a distal end segment each having a proximal end and a distal end and each having the general shape of a frustrum of a cone, the distal end of the proximal end segment being joined to the proximal end of the proximal spheroid segment and the proximal end of the distal end segment being joined to the distal end of the distal spheroid segment.

7. The balloon and stent of claim 6 wherein the proximal end segment of the balloon is a proximal dual conical end segment having a proximal end and a distal end and the distal end segment is a distal dual conical end segment having a proximal end and a distal end, the distal end of the proximal dual conical end segment being joined to the proximal end of the balloon's proximal spheroid segment and the proximal end of distal dual conical end segment being joined to the distal end of balloon's distal spheroid segment, each dual conical end segment being characterized by having the shape of a first frustum of a cone that makes an angle "C" with the balloon's longitudinal axis, and a second frustum of a cone that makes an angle "B" with the balloon's longitudinal axis, the angle "C" being greater than the angle "B".

8. The balloon and stent of claim 6 wherein the stent is mounted on that portion of the balloon that includes the proximal spheroid segment, the central segment and the distal spheroid segment, the stent having a proximal end that is placed within 1.0 mm from the proximal end of the proximal spheroid segment and the stent having a distal end that is placed within 1.0 mm from the distal end of the distal spheroid segment.

* * * * *